(12) United States Patent
Hochberg

(10) Patent No.: US 9,315,539 B2
(45) Date of Patent: Apr. 19, 2016

(54) 11 BETA-SHORT CHAIN SUBSTITUTED ESTRADIOL ANALOGS AND THEIR USE IN THE TREATMENT OF MENOPAUSAL SYMPTOMS AND ESTROGEN SENSITIVE CANCER

(75) Inventor: Richard Hochberg, Guilford, CT (US)

(73) Assignee: YALE UNIVERSITY, New Haven, CT (US)

(*) Notice: Subject to any disclaimer, the term of this patent is extended or adjusted under 35 U.S.C. 154(b) by 669 days.

(21) Appl. No.: 10/676,287

(22) Filed: Oct. 1, 2003

(65) Prior Publication Data
US 2004/0142915 A1 Jul. 22, 2004

Related U.S. Application Data

(60) Provisional application No. 60/415,079, filed on Oct. 1, 2002.

(51) Int. Cl.
*A61K 31/56* (2006.01)
*C07J 1/00* (2006.01)
*A61K 31/567* (2006.01)

(52) U.S. Cl.
CPC . *C07J 1/00* (2013.01); *A61K 31/567* (2013.01)

(58) Field of Classification Search
CPC .................................................. A61K 31/567
USPC .......................................... 514/182; 552/629
See application file for complete search history.

(56) References Cited

U.S. PATENT DOCUMENTS

| 3,972,906 | A | * | 8/1976 | van den Broek et al. | 552/617 |
| 4,617,298 | A | * | 10/1986 | Bodor et al. | 514/176 |
| 6,268,361 | B1 | * | 7/2001 | Palkowitz | 514/231.2 |
| 2001/0025051 | A1 | * | 9/2001 | Cameron et al. | 514/422 |

FOREIGN PATENT DOCUMENTS

| WO | WO00/31112 | 6/2000 |
| WO | WO0031112 | 6/2000 |

OTHER PUBLICATIONS

Agarwal et al., "Hormone-hormone antagonism in glucocorticoid action in vivo." Antihormones, 1979, pp. 51-73, (Abstract only).*
Goodman and Gilman, 1985, seventh edition, pp. 1421-1423.*
Jelinkova et al., "A quantitative test for oestrogenic activity using rat endometrium lactate dehydrogenase.", Acta Endocrinologica, vol. 96, pp. 389-393, 1981.*
Zhang, Jing—xin et al., J. Med. Chem. 2005, 48, 1428-1447.
Jelinkova, Marta et al., Acta Endocrinologica 1981, 96, 389-993.

* cited by examiner

*Primary Examiner* — Barbara P Badio
(74) *Attorney, Agent, or Firm* — Henry D. Coleman; R. Neil Sudol

(57) ABSTRACT

The present invention relates to novel 11-β estradiol ester compounds and their use as locally active estrogens in the treatment of the symptomology of menopause and to treat estrogen sensitive cancers, including breast cancer.

29 Claims, 14 Drawing Sheets

ICI 164,384

RU39411

Tamoxifen

Raloxifene

E11-2,1

E11-2,2

Estrogen Receptor Competition assay

*in vivo* Uterotrophic Assay

Figure 8 Exemplary Compounds of the Present Invention

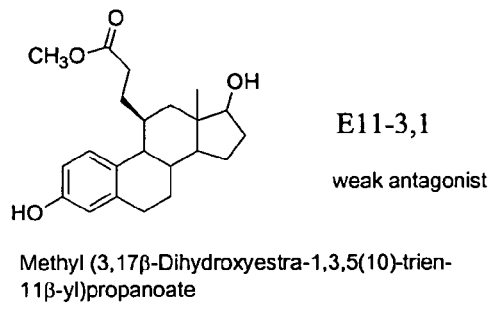

E11-3,1 weak antagonist

Methyl (3,17β-Dihydroxyestra-1,3,5(10)-trien-11β-yl)propanoate

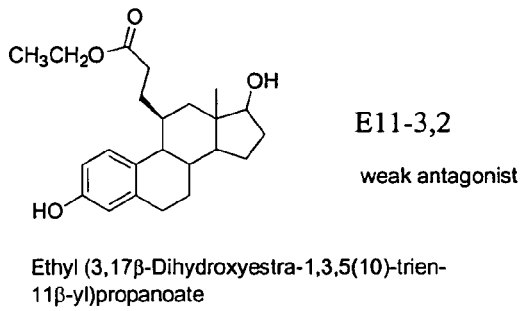

E11-3,2 weak antagonist

Ethyl (3,17β-Dihydroxyestra-1,3,5(10)-trien-11β-yl)propanoate

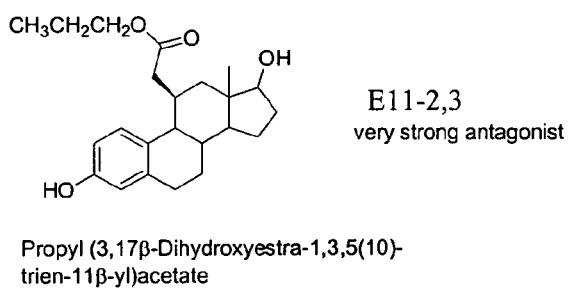

E11-2,3 very strong antagonist

Propyl (3,17β-Dihydroxyestra-1,3,5(10)-trien-11β-yl)acetate

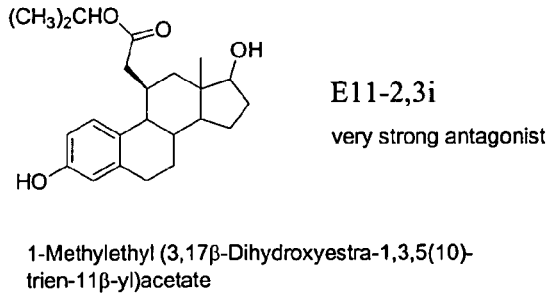

E11-2,3i very strong antagonist

1-Methylethyl (3,17β-Dihydroxyestra-1,3,5(10)-trien-11β-yl)acetate

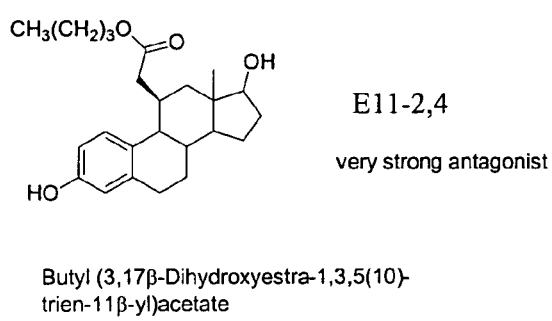

E11-2,4 very strong antagonist

Butyl (3,17β-Dihydroxyestra-1,3,5(10)-trien-11β-yl)acetate

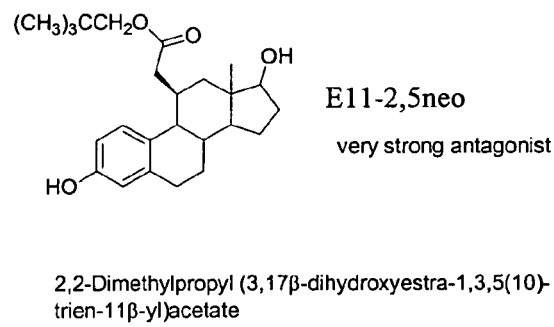

E11-2,5neo very strong antagonist 2,2-Dimethylpropyl (3,17β-dihydroxyestra-1,3,5(10)-trien-11β-yl)acetate E11-1,2Rev
agonist (3,17β-Dihydroxyestra-1,3,5(10)-trien-11β-yl)
methyl acetate E11-2,2Rev
agonist 2'-(3,17β-Dihydroxyestra-1,3,5(10)-trien-11β-yl)
ethyl acetate E11-3,2Rev
antagonist 3'-(3,17β-Dihydroxyestra-1,3,5(10)-trien-11β-yl)
propyl acetate E11-3,piv Rev
antagonist 3'-(3,17β-Dihydroxyestra-1,3,5(10)-trien-11β-yl)
propyl trimethylacetate E11-1,2ether
agonist 11β-(Ethoxymethyl)estra-1,3,5(10)-trien-
3,17β-diol E11-2,2ether
strong antagonist 11β-(2-Ethoxyethyl)estra-1,3,5(10)-trien-
3,17β-diol E11-2K2
weak agonist 1-(3,17β-Dihydroxyestra-1,3,5(10)-trien-11β-yl)
butan-2-one E11-2K3
antagonist 1-(3,17β-Dihydroxyestra-1,3,5(10)-trien-11β-yl)
pentan-2-one E11-2S,2
antagonist O-Ethyl (3,17β-dihydroxyestra-1,3,5(10)-trien-
11β-yl)thioacetate

SCHEME I

SCHEME 2

SCHEME 3

SCHEME 4

SCHEME 5

11 BETA-SHORT CHAIN SUBSTITUTED ESTRADIOL ANALOGS AND THEIR USE IN THE TREATMENT OF MENOPAUSAL SYMPTOMS AND ESTROGEN SENSITIVE CANCER

RELATED APPLICATIONS

This application claims the benefit of priority from provisional application Ser. No. 60/415,079, filed Oct. 1, 2002.

GOVERNMENT RIGHTS STATEMENT

This invention was made with government support under grant numbers CA 37799 and HL061432 awarded by the NIH. The government has certain rights in the invention.

FIELD OF THE INVENTION

The present invention relates to novel 11-β estradiol ester compounds and their use as locally active estrogens or competitors of estrogen in the treatment of the symptomology of menopause and to treat estrogen sensitive cancers, including breast cancer.

BACKGROUND OF THE INVENTION

In recent years estrogen antagonists have become extremely important therapeutic agents for a variety of symptoms of the menopause as well as for the treatment of estrogen sensitive cancers, such as breast cancer. There are a 2 major types of estrogen antagonists.

1) the pure antiestrogens, which are typified by analogs of estradiol, substituted at C-7α-(ICI 164,384) and C-11β (RU39411). These two examples are shown in attached FIG. 1.

2) The Selective Estrogen Receptor Modulators (SERMS). These compounds have some of the structural features of the potent estrogen, diethylstilbestrol: two examples are shown in attached FIG. 2.

The SERMS are unusual antiestrogens, in that they are antiestrogenic in specific tissues, such as the uterus, breast, vagina as well as the brain, while they are estrogenic in other estrogen target organs, such as bone, liver and blood vessels. Consequently, the SERMS maintain bone density and lower blood levels of cholesterol and LDL while raising HDL. Both the pure antiestrogens and the SERMS exert their effects through the estrogen receptor, each through very different mechanisms. However, as can be seen from their structures above they share some structural features, mainly long and bulky side chains that are usually charged either with tertiary amines or carboxylic groups.

Recently the inventor has been working on the design and synthesis of locally active estrogens, "soft estrogens" that could be used for local administration to treat vaginal dyspareunia caused by the menopause or through antiestrogen therapy. These compounds were designed to be metabolically labile so that they would be destroyed rapidly in tissues and blood, thus, acting only at the site of administration, having no or little systemic action. These were structure—activity studies, in which we produced carboxylic analogs (and their esters) of different chain lengths and at different positions in the nucleus of estradiol. The theory was to produce compounds in which the carboxylic acid derivatives of estradiol are inactive while the esters are active, thus the esters are rapidly inactivated by the ubiquitous non-specific esterases. Thus, we synthesized carboxylic ester analogs at 7α-, 11β-, 15α-, and 16α-, positions in the steroid nucleus that the estrogen receptor can tolerate somewhat bulky substituents.

All of these compounds were tested in various estrogen responsive models: estrogen receptor binding by competition; estrogen potency in the Ishikawa endometrial cell; in vivo assays in rodents, local—vaginal activity, systemic—uterotrophic activity; as well as substrates for esterase activity. In general the results were unremarkable and several of the compounds have the desired properties for local therapeutic action. However, the carboxylate esters at the 11β-position gave unexpected results.

OBJECTS OF THE INVENTION

It is an object of the invention to provide novel compounds and pharmaceutical compositions for use in treating the symptomology of menopause, physiological effects which occur secondary to menopause such as osteoporosis (by maintaining bone density) and risks for cardiovascular disease (by lowering blood levels of cholesterol and LDL while raising HDL), as well as estrogen-sensitive cancers, such as breast cancer.

It is yet another object of the invention to provide methods for treating the symptomology of menopause, especially including osteoporosis, and reducing the risks for cardiovascular disease by lowering blood levels of cholesterol and LDL while raising HDL), as well as treating estrogen-sensitive cancers.

It is still a further object of the present invention to provide novel compounds and compositions which may be used in a prophylactic manner to reduce the likelihood of the occurrence or recurrence of estrogen-sensitive breast cancer in a patient and/or cardiovascular disease which occurs secondary to menopause.

These and/or other objects of the present invention may be readily gleaned from the description of the invention which follows.

BRIEF DESCRIPTIONS OF THE INVENTION

Figure 1:
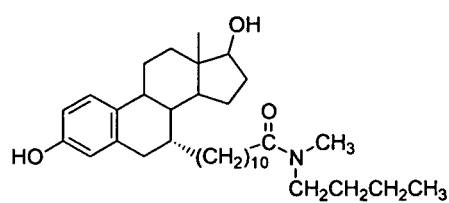
FIG. 1 exemplifies two examples of the pure antiestrogens, which are typified by analogs of estradiol.
Figure 1:
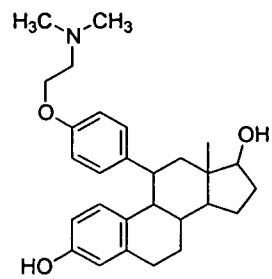

The present invention relates to estradiol compounds according to the chemical structure:

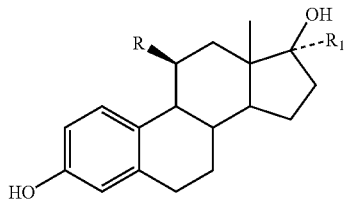

Where R is a

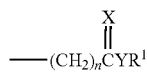

group, a

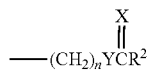

group, a

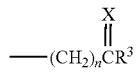

group, or a —$(CH_2)_nXR^4$ group,
$R^1$, $R^2$, $R^3$ and $R^4$ are each independently a $C_1$-$C_6$ linear, branch-chained or cyclo-alkyl group, preferably a $C_1$-$C_5$ linear, branch-chained or cyclo-alkyl group, more preferably a $C_1$-$C_4$ linear or branch-chained alkyl group;
$R_1$ is H, $CH_3$, a vinyl group (—CH=$CH_2$), or an ethynyl group (—C≡CH);
X is O or S and Y is O (preferably, X is O), and
n is from 1 to 3.

The present invention also relates to pharmaceutical compositions according to the present invention comprising an effective amount of at least one compound as described above in combination with a pharmaceutically acceptable carrier, additive or excipient. Preferably, pharmaceutical compositions according to the present invention are formulated in topical or oral dosage form for administration to the patient.

In another aspect of the present invention, a therapeutic treatment comprises administering one or more of the active compounds according to the present invention to a patient in need of therapy for the treatment of the symptomology associated with menopause, especially including osteoporosis, or elevated cholesterol and/or LDL levels. Estrogen-sensitive cancers may also be treated using effective amounts of one or more compounds according to the present invention. Preferred aspects of the present invention include the treatment of estrogen-sensitive breast cancer. Prophylactic aspects of the present invention are also contemplated by the present invention. A particularly preferred prophylactic aspect of the present invention relates to the use of the present compounds to reduce the likelihood of the occurrence or recurrence of estrogen-sensitive breast cancer.

DETAILED DESCRIPTION OF THE INVENTION

The following terms shall be used throughout the specification to describe the present invention.

The term "patient" is used throughout the specification to describe an animal, preferably a human, to whom treatment, including prophylactic treatment, with the compounds according to the present invention is provided. For treatment of the symptomology, conditions or disease states which are specific for a specific animal such as a human patient, the term patient refers to that specific animal. In most instances in the present invention, the patient is a human female exhibiting symptomology associated with menopause or is an estrogen-sensitive cancer patient, more likely a female breast cancer patient.

The term "effective amount" is used throughout the specification to describe concentrations or amounts of compounds according to the present invention which may be used to produce a favorable change in the symptomology, disease or condition treated, whether that change is a decrease in or reversal of the effects of symptomology or disease state depending upon the disease state or condition treated. In the present invention, in preferred aspects, an effective amount is that amount which is used to treat the symptomology associated with menopause, in its most preferred aspect, osteoporosis or alternatively, breast cancer. An effective amount for purposes of treating one or more disease states or symptoms of the present invention, includes the timing and manner in which an active compound is administered to a patient.

The term "alkyl" is used throughout the specification to describe a hydrocarbon radical containing between one and six carbon units, more preferably between one and five carbon units, preferably one and four carbon units. Alkyl groups for use in the present invention include linear, branched-chain groups and cycloalkyl groups such as methyl, ethyl, propyl, i-propyl, butyl, sec-butyl, tert-butyl, pentyl, neo-pentyl, cyclopropyl, cyclopentyl, etc.

The term "menopause" is used throughout the specification to describe the period in a woman's life between the ages of approximately 45 and 50 after which menstruation (menses) naturally ceases. The symptomology associated with menopause which is particularly relevant to the present invention includes bone loss associated with osteoporosis, elevated cholesterol and LDL and cardiovascular disease, among others.

The term "estrogen-sensitive cancer" is used throughout the specification to describe a type of cancer, more specifically, breast cancer, which may be sensitive to the administration of estrogen.

A preferred therapeutic aspect according to the present invention relates to methods for treating the symptomology of menopause comprising administering therapeutically effective amounts or concentrations of one or more of the compounds according to the present invention to treat the symptomology associated with menopause in the patient. This symptomology includes bone loss associated with osteoporosis, as well as increased blood levels of cholesterol and LDL. In each of these cases, the preferred oral route of administration of compounds according to the present invention may take maximum advantage of the effects of the compounds in vivo.

Alternative methods according to the present invention include the administration of effective amounts of one or more compounds according to the present invention to treat or reduce the likelihood of the occurrence or recurrence of breast cancer in a patient.

Pharmaceutical compositions based upon these novel chemical compounds comprise the above-described compounds in an effective amount for the treatment or prophylaxis of the symptomology of menopause or a related condition or disease state including estrogen-sensitive breast cancer, optionally in combination with a pharmaceutically acceptable additive, carrier or excipient. Pharmaceutical compositions in oral dosage form are particularly preferred and topical dosage form for local delivery of the active compounds, in creams, gels and lotions, are also preferred.

Certain of the compounds, in pharmaceutical dosage form, may be used as prophylactic agents for preventing or reducing the likelihood of a patient exhibiting specific symptomology associated with menopause such as osteoporosis and/or cardiovascular disease by reducing blood levels of cholesterol and/or LDL or to reduce the likelihood of an occurrence or recurrence of breast cancer. Effective amounts of compounds according to the present invention in pharmaceutical dosage form optionally in combination with a pharmaceutically acceptable carrier, additive or excipient are contemplated in this aspect of the present invention.

Modifications of the active compound can affect the solubility, bioavailability and rate of metabolism of the active species, thus providing control over the delivery of the active species. Further, the modifications may affect the activity of the compound, in some cases increasing the activity over the parent compound. This can easily be assessed by preparing the derivative and testing its activity according to known methods well within the routineer's skill in the art.

The compounds of this invention may be incorporated into formulations for all routes of administration including for example, oral and parenteral including intravenous, intramuscular, intraperitoneal, intrabuccal, transdermal and in suppository form. Oral dosage forms are most preferred and topical dosage forms such as creams, lotions, gels and suppositories which can be delivered to specific sites of the body may be preferred for use in the present invention.

Pharmaceutical compositions based upon these novel chemical compounds comprise the above-described compounds in an effective amount for treating the symptomology of menopause which have been described hereinabove, especially including osteoporosis or to reduce the likelihood that elevated blood levels of cholesterol and/or LDL will result in cardiovascular disease or to treat breast cancer therapeutically or prophylactically, optionally in combination with a pharmaceutically acceptable additive, carrier and/or excipient. One of ordinary skill in the art will recognize that an effective amount of one of more compounds according to the present invention will vary with the condition or symptomology to be treated or prevented, its severity, the treatment regimen to be employed, the pharmacokinetics of the agent used, as well as the patient to be treated.

In the pharmaceutical aspect according to the present invention, the compound according to the present invention is formulated preferably in admixture with a pharmaceutically acceptable carrier. In general, it is preferable to administer the pharmaceutical composition in orally administrable form, especially tablets and/or hard or soft gelatin capsules, but a number of formulations may be administered via a topical route with, for example, creams, gels, lotions and suppositories or by parenteral, intravenous, intramuscular, transdermal, buccal, subcutaneous or other route. Intravenous and intramuscular formulations, when used, are administered in sterile saline. Of course, one of ordinary skill in the art may modify the formulations within the teachings of the specification to provide numerous formulations for a particular route of administration, if desired, without rendering the compositions of the present invention unstable or compromising their therapeutic activity, noting that the ester groups (R) may be somewhat labile. In particular, the modification of the present compounds to render them more soluble in water or other vehicle, for example, may be accomplished by minor modifications which are well within the ordinary skill in the art. It is also well within the routineer's skill to modify the route of administration and dosage regimen of a particular compound in order to manage the pharmacokinetics of the present compounds for maximum beneficial effect to the patient.

The amount of compound included within therapeutically active formulations according to the present invention is an effective amount for treating the symptom or condition. In its most preferred embodiments, the present compounds are administered orally for treating the symptomology of osteoporosis or to treat or reduce the likelihood of an occurrence or recurrence of breast cancer. In general, a therapeutically effective amount of the presently preferred compound in dosage form usually ranges from slightly less than about 0.001 mg./kg. to about 0.1 g./kg., preferably about 0.01 mg/kg to about 0.1 mg/kg of the patient or considerably more depending upon the compound used, the condition or symptomology treated and the route of administration, although exceptions to this dosage range may be contemplated by the present invention and are well within the teachings of the present invention.

Administration of the active compound preferably occurs via an oral route, using tablets or hard or soft gelatin capsules, but also may occur by other routes including a topical dosage route, and in particular, via a cream, gel, lotion or suppository. In certain aspects, administration may range from continuous drip to oral administration and may include oral, topical, parenteral, intramuscular, intravenous, subcutaneous, transdermal (which may include a penetration enhancement agent) and buccal routes of administration, among other routes of administration. Other routes of administration include local delivery at the site of administration, for example, from an implanted material (such as an artificial hip or other prosthesis), among others. Preferably, the active compounds are administered via an oral route of administration or alternatively by a topical route, preferably as creams, gels, lotions or suppositories for administration to the patient.

To prepare the pharmaceutical compositions according to the present invention, an effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., topical, oral or parenteral, preferably topical. In preparing pharmaceutical compositions in the preferred topical dosage form, any of the usual pharmaceutical media may be used including thickeners, emollients, emulsifiers, etc. may be used to produce creams, gels, salves, ointments and the like for topical delivery to the patient. Alternatively, a patch for transdermal delivery may be used.

In the case of oral dosage forms, liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

The present compounds may be used to treat animals, and in particular, mammals, especially including humans, as patients. Patients may be treated by administering to the patient an effective amount of one or more of the compounds according to the present invention optionally in a pharmaceutically acceptable carrier or diluent, either alone, or in combination with other known pharmaceutical agents, depending upon the condition or symptomology to be treated. This treatment can also be administered in conjunction with other conventional therapies, including the administration of taxophen and other agents for treatment and/or prophylaxis of breast cancer.

The active compound is included in the pharmaceutically acceptable carrier or diluent in an amount sufficient to deliver to a patient a therapeutically effective amount for the desired indication, without causing toxic effects in the patient treated.

The compound is conveniently administered in any suitable unit dosage form in an effective amount, including but not limited to one containing less than 1 mg (preferably, at least 1 mg) to 500 mg (usually well below the upper range), preferably 5 to 300 mg of active ingredient per unit dosage form. A topical dosage form, including through a transdermal patch ranging from about 5 to about 250 mg is usually convenient.

The concentration of active compound in the drug composition will depend on absorption, distribution, inactivation, and excretion rates of the drug as well as other factors known to those of skill in the art. It is to be noted that dosage values will also vary with the severity of the condition or symptomology to be treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time. In its most preferred aspect of the present invention, i.e., in the oral administration of compounds according to the present invention to the patient to be treated, the active may be administered as infrequently as once every several days to several times a day, depending upon the activity of the compounds and other factors well known in the art.

Oral compositions, if used, will generally include an inert diluent or an edible carrier. They may be enclosed in gelatin capsules (soft or hard) or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The active compound may also be administered as a component of an elixir, suspension, syrup, wafer, chewing gum or the like. A syrup may contain, in addition to the active compounds, sucrose and/or corn syrup as a sweetening agent and certain preservatives, dyes and colorings and flavors.

The active compound can also be mixed with other active materials which do not impair the desired action, or with materials which supplement the desired action, such as other hormonal agents, and in other instances depending upon the desired therapy or target, other pharmaceutically active compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. If administered intravenously, preferred carriers include, for example, physiological saline or phosphate buffered saline (PBS). In the case of the preferred pharmaceutical compositions in topical dosage forms, creams, gels and/or viscous lotions may be used as vaginal delivery forms. Creams, gels, lotions and suppositories may be formulated using standing pharmaceutical procedures.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid, among others. Methods for preparation of such formulations are well known and will be readily apparent to those skilled in the art.

Liposomal suspensions may also be pharmaceutically acceptable carriers. These may be prepared according to methods known to those skilled in the art. For example, liposome formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

Compounds according to the present invention may be readily prepared using chemical synthetic techniques which are well-known in the art. These syntheses are exemplified in the accompanying experimental text and in FIGS. 9-13, Schemes 1-5. Although the presentation is of exemplary chemistry, it is recognized that one of ordinary skill in the art may utilize the teachings of the present invention or modify the procedures otherwise disclosed herein in a manner which enables the routine practice of the present invention. Analogous compounds may be readily synthesizes by adapting the specific methodology disclosed and applying well known synthetic organic chemistry techniques well know in the art.

The following non-limiting examples are provided to exemplify the present invention. One of ordinary skill will recognize that the presentation of these examples for purposes of exemplary teachings of the present invention and is not be construed as limiting the breadth of the invention in any way.

Examples

Figure 9:
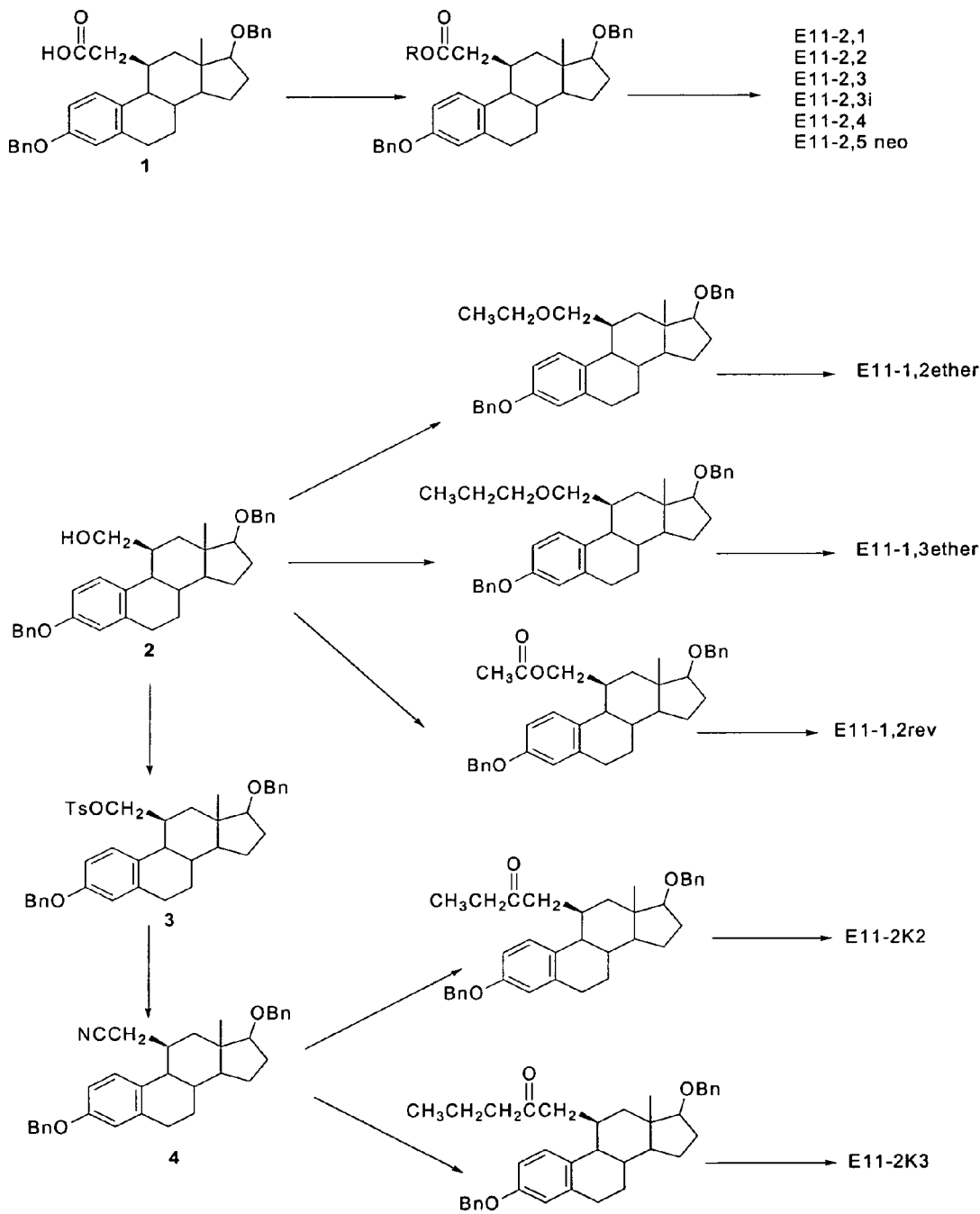
FIGS. 9-13, presents chemical synthetic schemes for synthesizing a number of compounds according to the present invention.
Figure 10:
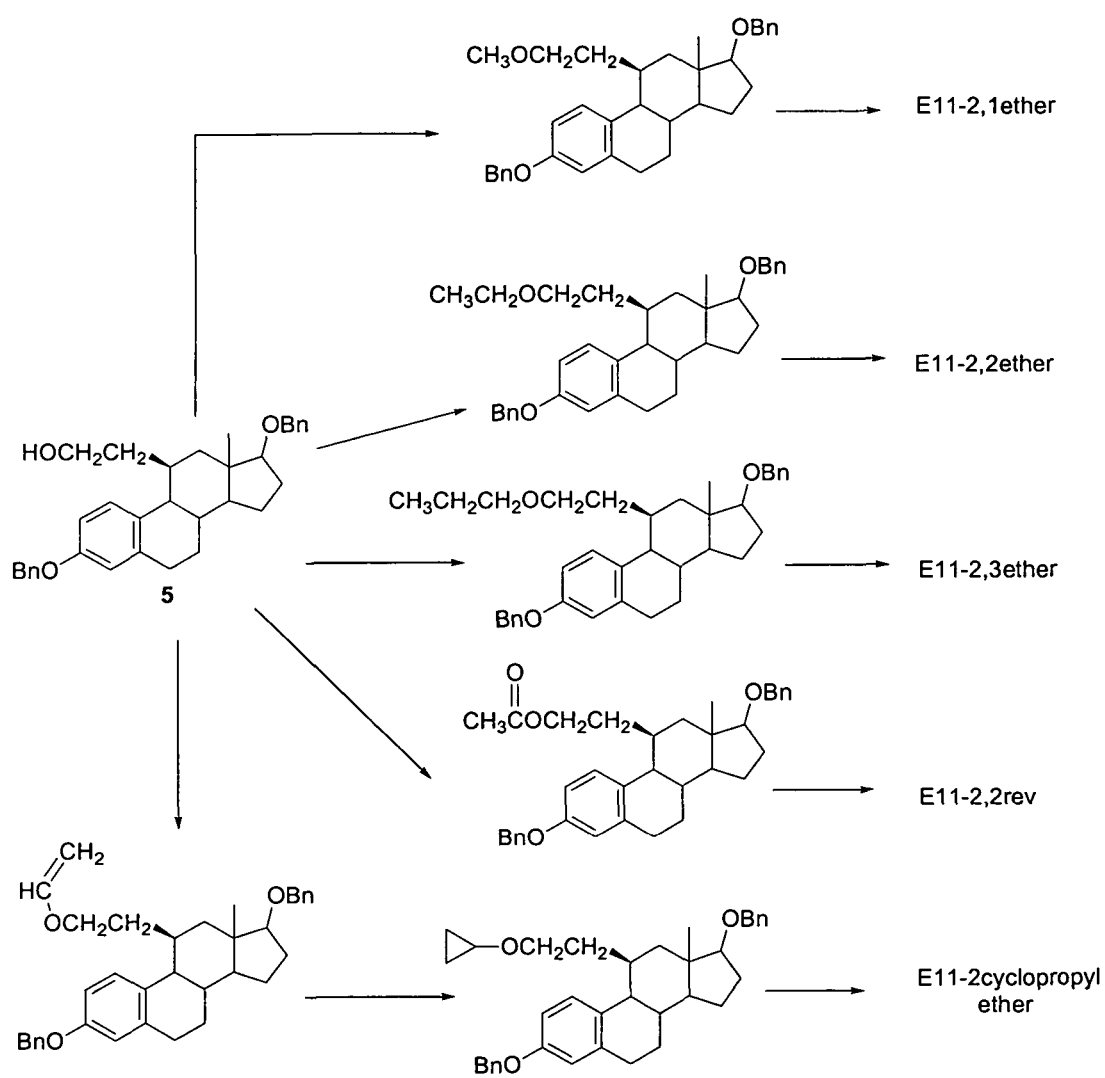
Figure 11:
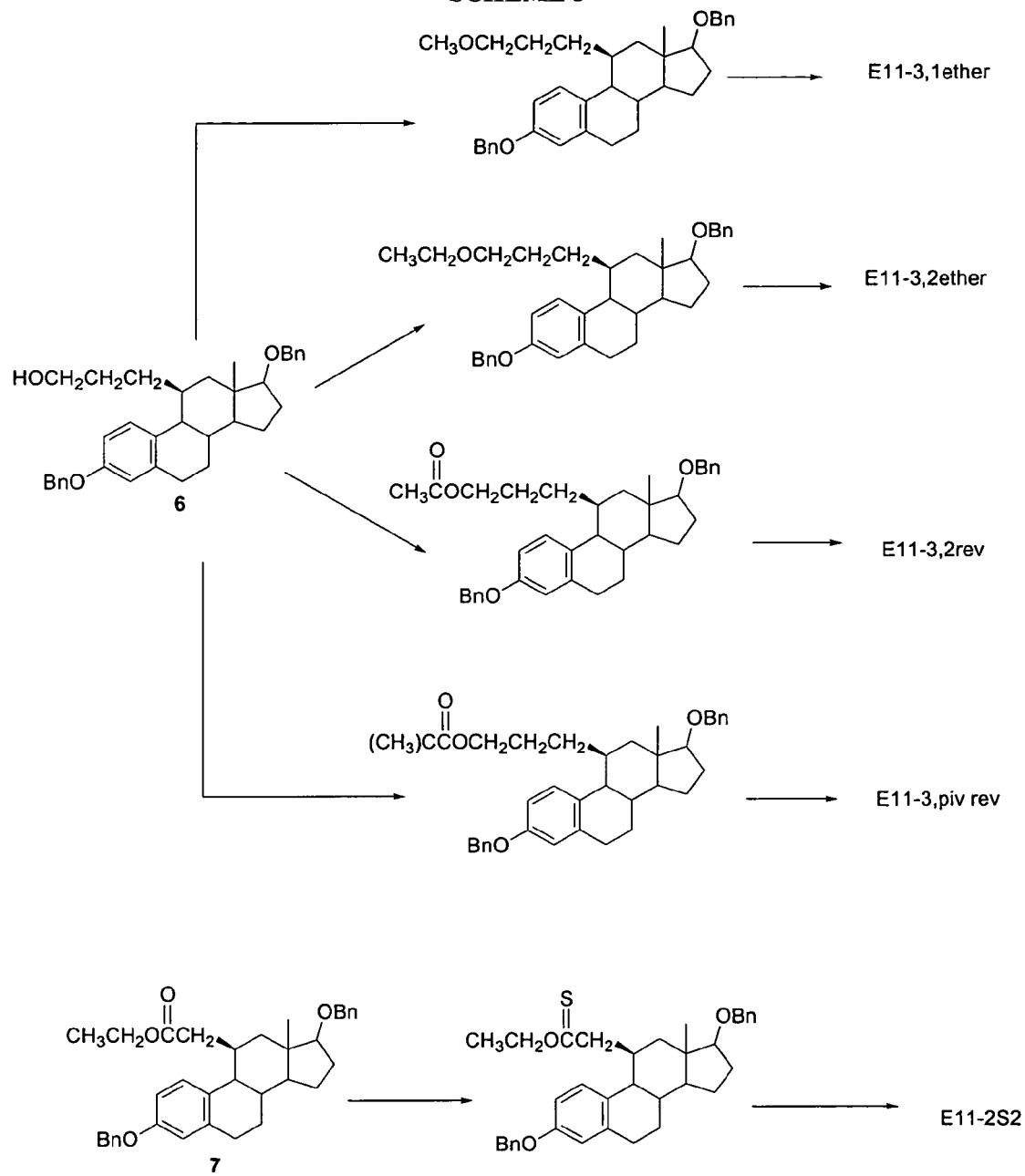
Figure 12:
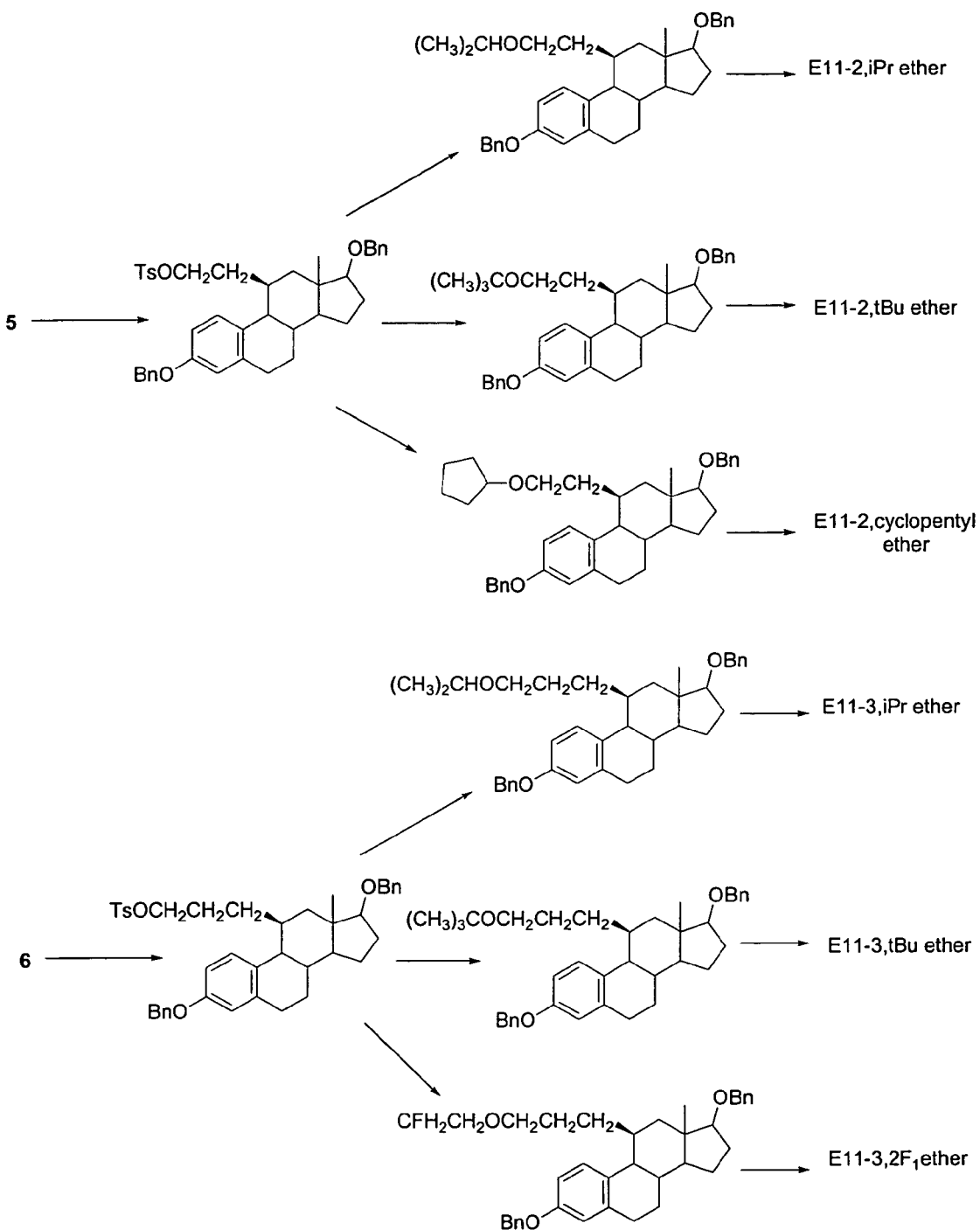
Figure 13:
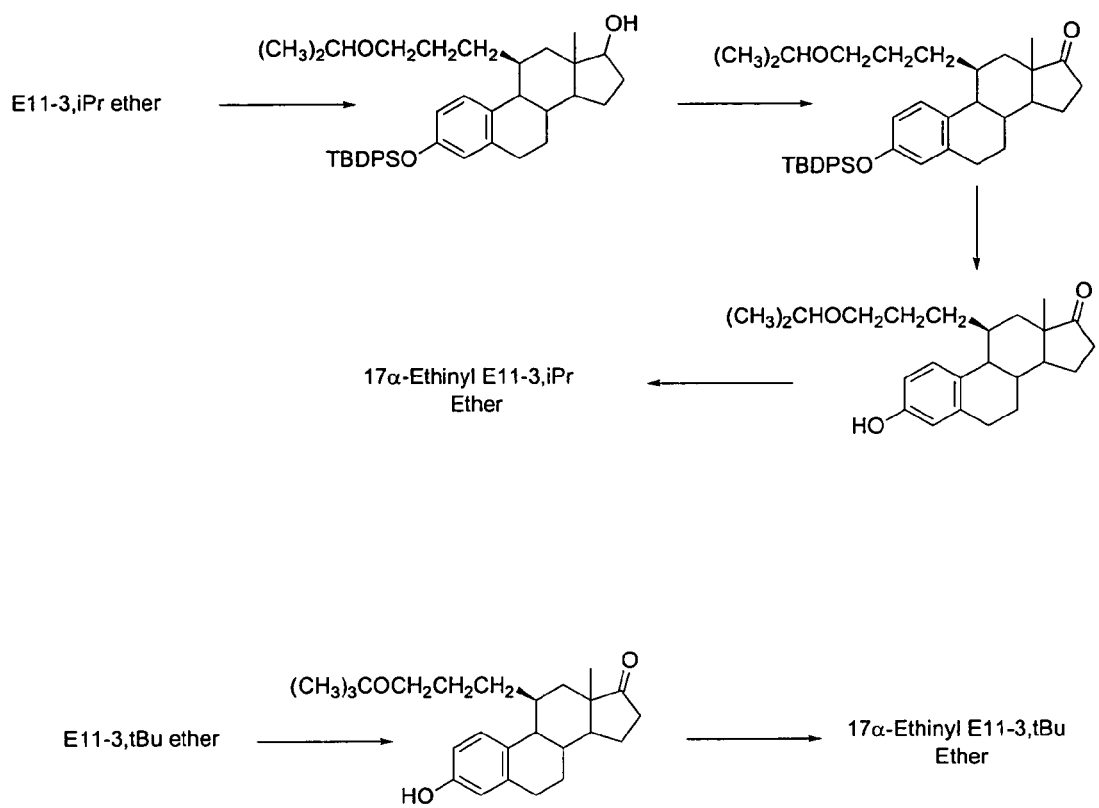

Chemical Synthesis (Following the General Schemes Set Forth in FIG. 9, Scheme I

Preparation of Compound 2

To a solution of 3,17β-dibenzyloxyestra-1,3,5(10)-trien-11-one (prepared as previously described in the literature) (0.52 g) in $Et_2O$ (15 mL) was added trimethylsilylmethylmagnesium chloride (15 mL, 1.0 M in ether). The solution was stirred at rt for 17 h, quenched with saturated aqueous $NH_4Cl$ (250 mL), and extracted with $CHCl_3$ (500 mL). The organic extract was washed with $H_2O$, dried over $MgSO_4$, and evaporated. The resulting white solid (0.7 g) was dissolved in a mixture of acetone (10 mL) and concentrated HCl (30 μL) and stirred at rt for 17 h. The mixture was evaporated to dryness with $N_2$ stream, dissolved in EtOAc (50 mL), washed with saturated aqueous $NaHCO_3$ and $H_2O$, dried over $Na_2SO_4$ and evaporated. Purification by flash chromatography using 15:1 hexanes/EtOAc as eluent gave 0.37 g of 3,17β-dibenzyloxy-11-methylene-estra-1,3,5(10)-triene. Hydroboration of the olefin (0.15 g) with $LiBH_4$ (10 mg) and catecholborane (1 mL, 1.0 M in THF) was carried out as described in the literature. The solution was stirred at rt for 18 h, added dropwise over 30 min to an ice-cold mixture of NaOH (0.15 g), water (0.5 mL), EtOH (1.5 mL) and $H_2O_2$ (35%, 1 mL). The solution was stirred at rt for 5 h and extracted with EtOAc. The combined organic extracts were washed with $H_2O$, dried over $Na_2SO_4$ and evaporated. Purification by flash chromatography using 20:1 $CH_2Cl_2$/EtOAc as eluent gave 110 mg of 2.

Preparation of Nitrile 4.

To a solution of 3,17-benzyl protected (1'-hydroxymethyl) estradiol 2 (200 mg) in pyridine (5 mL) was added pTsCl (400 mg) and the reaction was stirred at rt for 28 h, poured into saturated aqueous $NaHCO_3$ and extracted with EtOAc. Combined organic extracts were washed with $H_2O$, dried over $Na_2SO_4$, and evaporated. Purification by flash chromatography using hexanes/EtOAc 4:1 as eluent gave 200 mg of tosylated product 3. Tosylate 3 was stirred with NaCN (270 mg) in DMSO (14 mL) at 90° C. for 2 h, cooled to rt, and poured into saturated $NH_4Cl$. The mixture was extracted with $CH_2Cl_2$ and combined organic extracts were washed with $H_2O$, dried over $Na_2SO_4$ and evaporated. Purification by flash chromatography using hexanes/EtOAc 6:1 gave 140 mg of nitrile 4.

General Procedure for Preparation of E11,2-1, E11,2-2, E11, 2-3, E11,2-3i, E11,2-4 and E11,2-5 neo A mixture of 140 mg of nitrile 4, 700 mg KOH and ethylene glycol (5 mL) was heated at 140° C. for 5 days. The mixture was extracted with EtOAc (3×, 10 ml). The combined extracts were washed with $H_2O$, dried over $Na_2SO_4$ and evaporated. Purification by flash chromatography using 1:2 hexanes/EtOAc as eluent gave 34 mg of 1. A solution of the protected acid 1 (140 mg) in ethanol (25 mL) in the presence of $SOCl_2$ (700 μL) was stirred and heated at 50° C. for 2 h. The reaction was quenched with saturated aqueous $NaHCO_3$ solution and separated between EtOAc and water. The organic phase was washed, dried over $Na_2SO_4$, and concentrated in vacuo. Purification by flash chromatography using hexanes/EtOAc (6:1) gave 150 mg of protected ester 7. To a solution of 7 (100 mg) in $CH_2Cl_2$ (12 mL) at 0° C. was added, boron trichloride (4 mL of a 1M solution in $CH_2Cl_2$) and the reaction was stirred at 0° C. for 0.5 h. The reaction was quenched with saturated $NaHCO_3$ solution and separated between $CH_2Cl_2$ and $H_2O$. The organic phase was washed with $H_2O$, dried over $Na_2SO_4$, and concentrated in vacuo. Purification by flash chromatography using hexanes/EtOAc (2:1) followed by HPLC gave 35 mg of product (E11-2,2).

E11-2,1 was prepared in the same manner as E11-2,2 using methanol instead of ethanol.

E11-2,3 was prepared in the same manner as E11-2,2 using n-propanol instead of ethanol E11-2,3i was prepared in the same manner as E11-2,2 using isopropanol instead of ethanol E11-2,4 was prepared in the same manner as E11-2,2 using butanol instead of ethanol E11-2,5neo was prepared in the same manner as E11-2,2 using neopentyl alcohol instead of ethanol Preparation of E11-3,1 and E11-3,2.

Allylmagnesium bromide (2.5 mL, 1.0 M in ether) was added to a solution of 3,17β-dibenzyloxyestra-1,3,5(10)-trien-11-one (prepared as previously described in the literature) (0.12 g) in THF (2.5 mL) under $N_2$. The reaction was stirred at rt for 1.5 h, quenched with saturated aqueous $NH_4Cl$ (10 mL) and extracted with EtOAc (3×, 20 mL). The combined extracts were washed with $H_2O$, dried over $Na_2SO_4$ and evaporated. Purification by flash chromatography using 4:1 hexanes/EtOAc as eluent gave 98 mg of 11α-allyl-3,17β-dibenzyloxyestra-1,3,5(10)-triene-11β-ol. To a solution of 98 mg of the above 11β-alcohol in $CH_2Cl_2$ (10 mL) was added $HSiEt_3$ (1 mL). The mixture was cooled to 0° C. and $BF_3.Et_2O$ (2 mL) was added. The reaction was stirred at 0° C. for 40 min, washed with saturated aqueous $NaHCO_3$ followed by $H_2O$, dried over $Na_2SO_4$ and evaporated. Purification by flash chromatography using 20:1 hexanes/EtOAc as eluent gave 90 mg of 11β-allyl-3,17β-dibenzyloxyestra-1,3,5(10)-triene. Compound 6 was prepared by hydroxylation of the the above allyl compound (20 mg) with $LiBH_4$ (1.5 mg) and catecholborane (0.2 mL) as described for the preparation of 2. Purification by flash chromatography using 2:1 hexanes/EtOAc as eluent gave 16 mg of 6. A solution of 6 (40 mg), Jones' reagent (4 mL) in acetone 4 mL was stirred at 0° C. for 0.5 h then quenched with 1:1 v/v $MeOH:H_2O$ (1 mL). The mixture was extracted with EtOAc and combined organic extracts were washed with $H_2O$, dried over $Na_2SO_4$ and concentrated in vacuo. Purification by flash column chromatography using hexanes/EtOAc (4:1) gave 15 mg of protected acid, 3-(3,17β-dibenzyloxyestra-1,3,5(10)-triene-11β-yl) propanoic acid. To deprotect, $BCl_3$ (0.6 mL) was added to a one third aliquot of the solution of the above acid (15 mg) in $CH_2Cl_2$ (1.5 mL) at 0° C. and stirred for 40 min. This aliquot was treated with MeOH (0.5 mL) and stirred at rt for 3 h. The mixture was extracted with EtOAc, washed with $H_2O$, dried over $Na_2SO_4$ and purified by HPLC giving 2 mg of E11-3,1. E11-3,2 was prepared in the same manner as E11-3,1 using ethanol instead of methanol.

Preparation of E11-1,2ether (Scheme 1)

KH (35% suspension in oil, 75 mg) was washed with hexane, suspended in toluene (1 ml). 3,17-Benzyl protected (11-hydroxymethyl)estradiol 2 (85 mg) was added in 2 ml toluene at room temperature and the mixture was stirred for half an hour before iodoethane (50 μl) was added. The reaction was stirred for 4 hours. The mixture was separated between EtOAc and water. The organic phase was washed, dried over $Na_2SO_4$, and evaporated to afford a residue which was purified by flash column chromatography using hexanes/EtOAc 17:1 gave 30 mg of protected ether. Deprotection of 15 mg using boron trichloride and purification by flash column and reverse phase HPLC as above gave the final product E11-1,2ether (7 mg). E11-1,3ether was prepared in the same manner as E11-1,2ether from 42 mg of 2 using propyl iodide instead of iodoethane. Deprotection as above gave 7 mg of E11-1,3ether.

Preparation of E11-2K2 and E11-2K3 (Scheme 1)

To a solution of nitrile 4 (30 mg) in ether (1 ml) was added ethyl magnesium bromide (60 μL, of a 3M solution in $Et_2O$) and the reaction was stirred at rt overnight. To this was added HCl (1M, 1 ml) and the reaction was stirred vigorously at rt for 2 h, separated between EtOAc and water. The organic phase was washed with $H_2O$, dried over $Na_2SO_4$, and evaporated to afford a residue. Purification by flash column chromatography using hexanes/EtOAc 4:1 gave 23 mg of protected ketone. Deprotection of 20 mg of protected ketone using boron trichloride and further purification by flash column chromatography and reverse phase HPLC as above gave 9 mg of E11-2K2.

E11-2K3 was obtained from 15 mg of 4, propylmagnesium chloride (100 μL, 2M solution in ether) as above gave 11 mg protected ketone. Deprotection of 10 mg of the protected ketone and purification as above gave 7 mg of E11-2K3.

Preparation of E11,2-1 ether, E11,2-2ether, E11,2-3ether, E11-2,cyclopropyl ether, E11 3,1ether, and E11-3,2ether (Scheme 2 and 3)

3,17β-Bis(benzyloxy)-11β-ethenylestra-1,3,5(10)-triene (600 mg) was hydroborated as above for 2 giving 300 mg of 3,17β-dibenzyloxy-11β-(2'-hydroxyethyl)estra-1,3,5(10)-triene 5. Compound 5 (50 mg) was added at room temperature to a suspension of KH (30 mg) in toluene (1 ml) and the mixture was stirred for half an hour before iodomethane (50 μl) was added. The reaction was stirred for 4 hours. The mixture was separated between EtOAc and water. The organic phase was washed, dried over $Na_2SO_4$, and evaporated to afford a residue which was purified by flash column chromatography using hexanes/EtOAc 20:1 giving 54 mg of protected methyl ether. Deprotection of 20 mg of protected methyl ether using $BCl_3$ and further purification by flash column and HPLC gave the final product E11-2,1ether (7.2 mg).

E11-2,2ether was prepared as described for E11-2,1ether except that iodoethane was used giving 10 mg of the protected ether. Deprotection as above gave 4.6 mg E11-2,2ether.

E11-2,3ether was prepared from protected alcohol 5 (60 mg) as above using propyl iodide instead of iodomethane. Deprotection and purification as above gave 5 mg of E11-2,3ether.

E11-3,1ether was prepared from protected alcohol 6 (42 mg) as above. Deprotection and purification as above gave 6 mg of E11 3,1ether.

E11-3,2ether was prepared from protected alcohol 6 (50 mg) as above using iodoethane instead of iodomethane. Deprotection and purification as above gave 5 mg of E11-3,2ether.

E11-2,cyclopropyl ether. A solution of protected alcohol 5 (50 mg), mercury (II) acetate (13 mg) in ethyl vinyl ether (2 mL) was stirred and heated at 33° C. for 18 h. Reaction was poured into $H_2O$ and extracted with $Et_2O$. Organic layer was washed with brine, dried over $Na_2SO_4$ and concentrated in vacuo. Purification of the residue by flash chromatography using 15:1 hexanes/EtOAc gave 40 mg of protected vinyl ether.

A solution of the protected vinyl ether (40 mg) in 1 mg $Et_2O$ was stirred at rt as 80 μL of a 1M solution of diethylzinc in hexanes was added followed by a solution of diiodomethane (33 mg) in $Et_2O$ (500 μL). Reaction was stirred at rt for 18 h, quenched with saturated aqueous $NH_4Cl$ (1 mL) and extracted with $Et_2O$. Organic extract was concentrated in vacuo and purified by flash chromatography using 17:1 hexanes/EtOAc giving 30 mg of protected cyclopropyl ether. Deprotection using $BCl_3$ and purification as above gave 4 mg of E11-2,cyclopropyl ether.

Preparation of E11-2iPr ether, E11-2,tBu ether,E11-2,cyclopentyl Ether, E11-3,2$F_1$ Ether, E11-3,iPr Ether and E11-3,tBu Ether (Scheme 4)

A solution of protected alcohol 5 (68 mg), p-toluenesulfonyl chloride (390 mg) in pyridine (5 mL) was allowed to stand at 0° C. for 6 days. The reaction was poured into $H_2O$ and extracted with $CH_2Cl_2$. Combined organic extracts were dried over $Na_2SO_4$ and concentrated in vacuo. Purification of the residue by flash chromatography using 4:1 hexanes/EtOAc gave 60 mg of the protected tosylate.

A suspension of 35% dispersion of KH in oil (washed with hexanes), 173 mg of 18-crown-6, 48 μL of isopropanol in 500 μL of anhydrous toluene was stirred at rt for 10 min. To this was added a solution of 20 mg of the protected tosylate in 500 μL of toluene and the reaction was stirred and heated at 80° C. for 6 h. The reaction was poured into $H_2O$ and extracted with $CH_2Cl_2$. Combined organic extracts were dried over $Na_2SO_4$ and concentrated in vacuo. Purification by flash chromatography using 8:1 hexanes/EtOAc gave 17 mg of the protected ether.

A suspension of the protected ether (17 mg), 5% Pd on carbon (10 mg) in EtOAc (4 mL) was stirred under an atmosphere of hydrogen for 2 days. The reaction was filtered through a 1" plug of Celite and washed through with EtOAc. The filtrate was concentrated in vacuo and the residue was purified by flash chromatography using 1:1 hexanes/EtOAc followed by HPLC giving 4 mg of E11-21Pr ether.

E11-2 tBu ether was prepared as above from the protected tosylate (11 mg) using solid potassium t-butoxide (19 mg) instead of KH and isopropanol. Deprotection and purification as above gave 1 mg of E11-2 tBu ether.

E11-2,cyclopentyl ether was prepared as above from the protected tosylate (36 mg) using cyclopentanol instead of isopropanol. Deprotection and purification as above gave 11 mg of E11-2,cyclopentyl ether.

E11-3,2$F_1$ ether was prepared as above except using the tosylate (69 mg) obtained from the alcohol 6 and using 2-fluoroethanol instead of isopropanol. Deprotection and purification as above gave 11 mg of E11-3,2$F_1$ ether.

E11-3,iPr ether was prepared as above except using the tosylate (30 mg) obtained from the alcohol 6. Deprotection and purification as above gave 7 mg of E11-3,iPr ether.

E11-3,tBu ether was prepared as above except using the tosylate (61 mg) obtained from the alcohol 6 and using potassium t-butoxide instead of KH and isopropanol. Deprotection and purification as above gave 4 mg of E11-3,tBu ether.

Preparation of 17α-Ethynyl E11-3,iPr ether (Scheme 5) A solution E11-31Pr ether (16 mg), t-butyldiphenylsilyl chloride (120 μL), 4-(dimethylamino)pyridine (10 mg), and triethylamine (200 μL) in $CH_2Cl_2$ (1 mL) was stirred at rt for 18 h. Reaction was poured into $H_2O$ and extracted with EtOAc. Organic extracts were dried over $Na_2SO_4$ and concentrated in vacuo. Purification of the residue by flash chromatography using 2:1 hexanes/EtOAc gave 14 mg of protected ether.

A solution of 14 mg of protected ether, sodium acetate (1 mg), and pyridinium chlorochromate (8 mg), in $CH_2Cl_2$ (2 mL) was stirred at rt for 2 h, poured into $H_2O$ and extracted with EtOAc. Organic extracts were dried over $Na_2SO_4$ and concentrated in vacuo. Purification of the residue by flash chromatography using 4:1 hexanes/EtOAc gave 10 mg of ketone.

To a solution of 1M tetrabutylammonium flurroide in THF (1 ml) was added the above ketone (10 mg) and reaction was stirred at rt for 1.5 h. The reaction was poured into $H_2O$ and extracted with EtOAc. Organic extracts were dried over Na$_2$SO$_4$ and concentrated in vacuo. Purification of the residue by flash chromatography using 2:1 hexanes/EtOAc gave mg of deprotected ketone.

A solution of the above deprotected ketone (5 mg) in DMSO (2 mL) was stirred at rt as a solution of 18% sodium acetylide in xylenes (1 mL) was added over 5 min. Reaction was stirred at rt for 3.5 h, poured into saturated aqueous NH$_4$Cl and extracted with EtOAc. The organic extracts were dried over Na$_2$SO$_4$ and concentrated in vacuo. Purification of the residue by flash chromatography using 1:1 hexanes/EtOAc followed by HPLC gave 3 mg of 17α-Ethynyl E11-3, iPr ether.

Preparation of 17α-Ethynyl E11-3,tBu ether (Scheme 5) A solution of E11-3,tBu ether (22 mg), pyridinium chlorochromate (19 mg), sodium acetate (1.4 mg) in CH$_2$Cl$_2$ (1 mL) and Et$_2$O (1 mL) was stirred at rt for 44 h. Reaction was poured into H$_2$O and extracted with EtOAc. The organic extracts were dried over Na$_2$SO$_4$ and concentrated in vacuo. Purification of the residue by flash chromatography using 3:1 hexanes/EtOAc gave 5 mg of ketone.

A solution of the above ketone (5 mg) in DMSO (2 mL) was stirred at rt as a solution of 18% sodium acetylide in xylenes (1 mL) was added over 5 min. The reaction was stirred at rt for 3.5 h, poured into saturated aqueous NH$_4$Cl and extracted with EtOAc. The organic extracts were dried over Na$_2$SO$_4$ and concentrated in vacuo. Purification of the residue by flash chromatography using 2:1 hexanes/EtOAc followed by HPLC gave 2 mg of 17α-Ethynyl E11-3,tBu ether Preparation of E11-3,2rev, E11-1,2rev and E11-2,2rev (Scheme 1-3) A solution of protected alcohol 6 (30 mg) in pyridine (0.5 mL) and acetic anhydride (0.5 mL) was stirred at rt for 20 h. The mixture was separated between EtOAc and H$_2$O and the organic phase was washed with H$_2$O, dried over Na$_2$SO$_4$ and concentrated in vacuo. Purification by flash column chromatography using hexanes/EtOAc 4:1 gave 42 mg of protected acetate. Deprotection of 20 mg of the protected acetate with boron trichloride as above gave 8 mg of E11-3, 2rev after purification by flash column and HPLC.

E11-1,2rev was prepared as above from alcohol 1 (30 mg) giving 9 mg after deprotection and purification as above.

E11-2,2rev was prepared as above from alcohol 5 (22 mg) giving 4 mg after deprotection and purification as above.

E11-3,piv rev was prepared as above except using alcohol 6 (50 mg) and using pivaloyl chloride instead of acetic anhydride giving 8 mg after deprotection and purification as above Preparation of E11-2S,2 (Scheme 3) A solution of benzyl-protected ester 7 (30 mg), Lawsson's reagent (60 mg) in O-xylene (3 ml) was stirred and heated at 140-150° C. for 23 hours. The mixture was directly purified by flash column chromatography using hexane/EtOAc (25:1) as eluent gave 27 mg of protected product. Deprotection using boron trichloride and further purification as above gave 5 mg of E11-2S,2 after purification as above.

BIOLOGICAL EXPERIMENTS

A number of compounds synthesized during experiments to determine activity of estradiol analogs in the inventor's laboratory. They were tested in various estrogen responsive models: estrogen receptor binding by competition; estrogen potency in the Ishikawa endometrial cell; in vivo assays in rodents, local—vaginal activity, systemic—uterotrophic activity; as well as substrates for esterase activity. In general, the results were fairly straightforward and several of the compounds exhibited the desired properties for local therapeutic action. However, the carboxylate esters at 11β-gave decidedly unexpected results.

Figure 3:
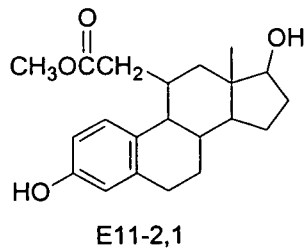
FIG. 3 shows two esterified compounds according to the present invention.
Figure 3:
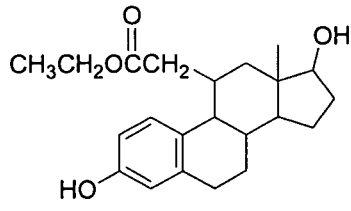

One of the series that synthesized in the inventor's laboratory was of the 11β-carboxymethyl compounds (our abbreviations show the carboxylic acid first and the alcohol portion second. i.e. E11-2,1 would be the methyl ester of the 11β-carboxymethyl estradiol, and E11-2,0 would be the free acid, etc. We tested the free acid and the methyl and ethyl esters E11-2,1 and E11-2,2 respectively, (FIG. 3.) in several of our screening tests.

Estrogen Receptor Competition Assay

Figure 4:
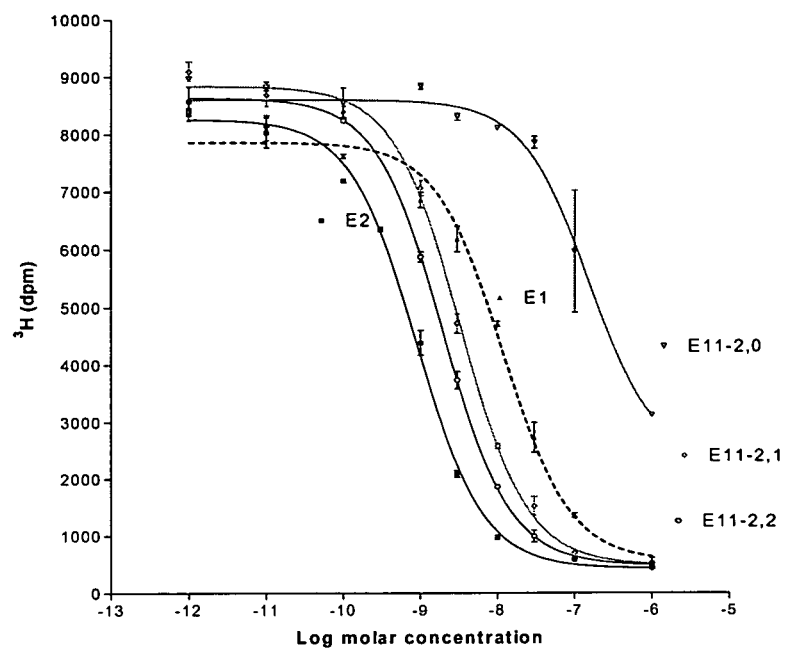
FIG. 4 shows the results of experiments performed to measure the binding affinity for the estrogen receptor by competition.

In the first of these experiments which measures the binding affinity for the estrogen receptor by competition we found that both E11-2,1 and E11-2,2 had very high affinity with a relative binding affinity (RBA) of 24% and 45% respectively. E11-2,0 had an RBA of 0.3% which is low albeit higher than the other carboxylates that we synthesized. The assay compares each ligand to estradiol (E2) which therefore has an affinity of 100%. For comparison, note that estrone (E1), one of the more active metabolites of estradiol has an RBA of only 9% in this assay. See FIG. 4, attached.

Ishikawa Estrogenic Potency Assay

Figure 5:
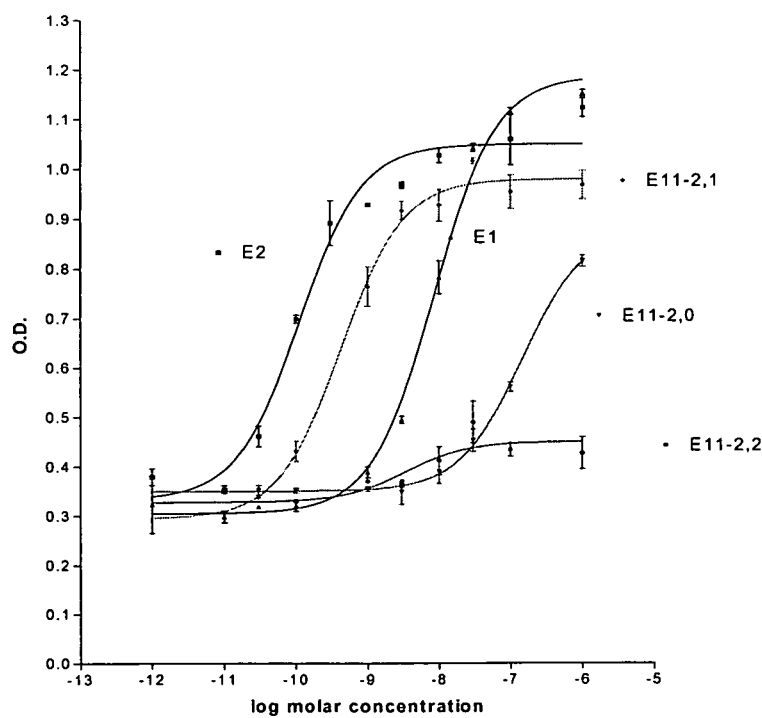
FIG. 5 shows the result of certain experiments in the Ishikawa Estrogenic Potency Assay.
Figure 6:
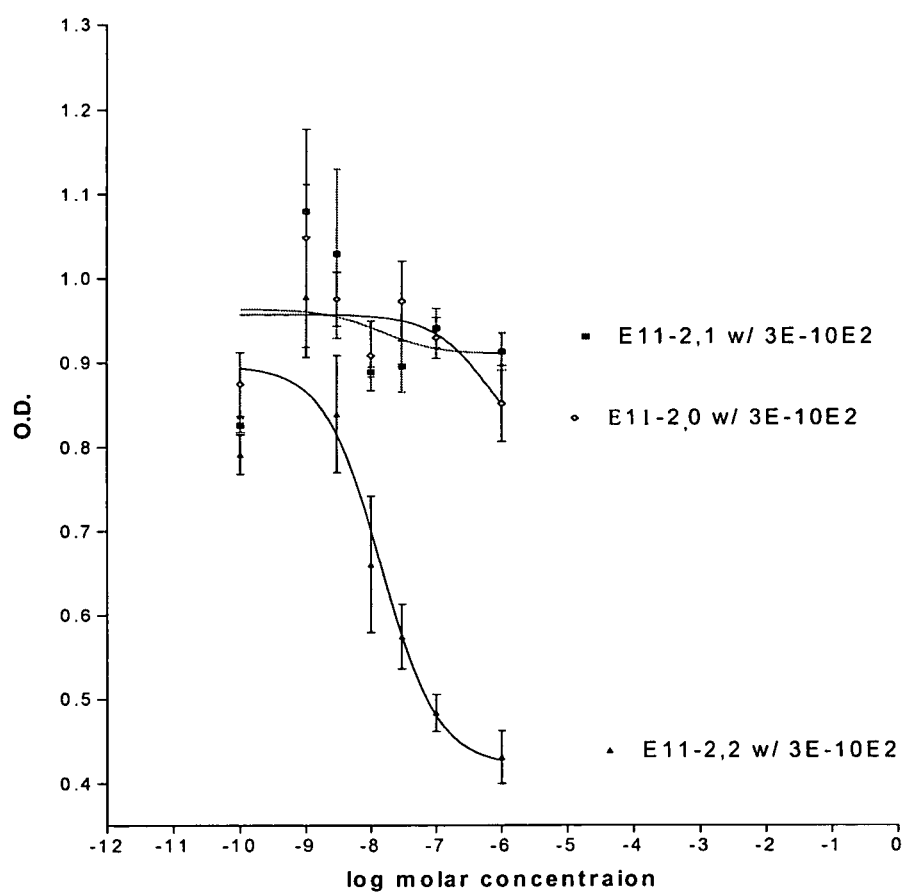
FIG. 6 shows the results of certain experiments using the Antiestrogen Ishikawa Cell Assay.

From the estrogen competition assay, we expected that the methyl and ethyl esters, E11-2,1 and E11-2,2 would have relatively high activity in the estrogen potency assay, induction of alkaline phosphatase in Ishikawa cells. However, the results were quite unexpected (see FIG. 5, attached). While E11-2,1 had a fairly high relative stimulatory activity (RSA) of 16% (again estradiol is set at 100% and for comparison estrone is 4%) E11-2,2 was almost inactive. In fact, E11-2,0 was more active than E11-2,2. We had never previously seen this disparity between estrogen receptor binding and biological activity. It occurred to us that we were observing the results that would obtained with a SERM and that E11-2,2 was in fact an antiestrogen. Consequently, we repeated the Ishikawa assay as an antiestrogenic assay (the assay is run in the presence of specified amounts of estradiol). As can be seen from the results in FIG. 6, attached, E11-2,2 inhibited the estrogenic stimulation of alkaline phosphatase in the Ishikawa cell, with very high potency. In several assays the Ki of E11-2,2 was approximately 1-2 nM. As would be expected from the estrogenic assay, neither E11-2,1 nor E11-2,0 showed any antiestrogenic activity.

Figure 2:
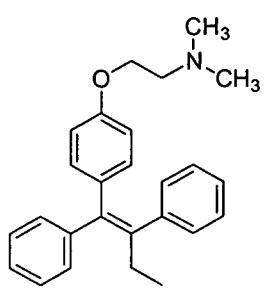
FIG. 2 exemplifies two examples of the selective estrogen receptor modulators, which typically have some of the structural features of typified by analogs of estradiol.
Figure 2:
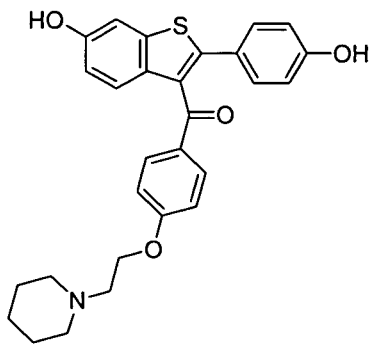

There are several notable aspects about these results. Most remarkable is the structure of the analog—a simple short chain ester. As can be seen in FIGS. 1 and 2, antiestrogens universally have a long, bulky and often charged sidechain. The ester is short and non-polar. The other highly unusual aspect of these results is the dramatic change from E11-2,1 as an estrogen to E11-2,2 as an antiestrogen. Thus, a complete reversal of function occurs with a single methylene group, by lengthening the side-chain from 4 to 5 atoms (non-hydrogen).

We continued our synthesis of various analogs in order to define the chemical characteristics that lead to antiestrogenic effects. In addition we were especially interested in synthesizing similar compounds as well as other compounds in which the 11β-sidechain contains some of the elements of the esters (ethers, ketones, thionoester) that do not have a labile ester function, in order to produce a SERM that might be longer lived and also be administered orally. In this regard, several compounds are described with a 17α-ethynyl group in order to protect the C-17 hydroxyl from biological oxidation. The results of this study are summarized in Table 1 and Table 2, below.

TABLE 1

| Structure | Label | Activity |
|---|---|---|
| 11β—CH$_2$CH$_2$COCH$_3$ (C=O) | E11-3,1 | antagonist |
| 11β—CH$_2$CH$_2$COCH$_2$CH$_3$ (C=O) | E11-3,2 | antagonist |
| 11β—CH$_2$COCH$_2$CH$_2$CH$_3$ (C=O) | E11-2,3 | strong antagonist |
| 11β—CH$_2$COCH(CH$_3$)$_2$ (C=O) | E11-2,3i | strong antagonist |
| 11β—CH$_2$COCH$_2$CH$_2$CH$_2$CH$_3$ (C=O) | E11-2,4 | strong antagonist |
| 11β—CH$_2$COCH$_2$C(CH$_3$)$_3$ (C=O) | E11-2,5neo | antagonist |
| 11β—CH$_2$OCCH$_3$ (C=O) | E11-1,2Rev | agonist |
| 11β—CH$_2$CH$_2$OCCH$_3$ (C=O) | E11-2,2Rev | agonist |
| 11β—CH$_2$CH$_2$CH$_2$OCCH$_3$ (C=O) | E11-3,2Rev | antagonist |
| 11β—CH$_2$CH$_2$CH$_2$OCC(CH$_3$)$_3$ (C=O) | E11-3,piv Rev | antagonist |
| 11β—CH$_2$CCH$_2$CH$_3$ (C=O) | E11-2K2 | weak agonist |
| 11β—CH$_2$CCH$_2$CH$_2$CH$_3$ (C=O) | E11-2K3 | antagonist |
| 11β—CH$_2$COCH$_2$CH$_3$ (C=S) | E11-2S2 | antagonist |

There are some strict structural requirements for the esters. For example changing the carboxylate to propionate from acetate reduces antagonism (E11-2,3 to E11-3,2). On the other hand changing the nature of the alcohol in the ester function retains antagonism, and in some cases decreases the Ki (increases potency). Some of the structural changes, cause steric inhibition of esterase and thereby increase the biological half-life (isopropyl, neopentyl). Interestingly, as seen in Table 1, reversing the acid and alcohol functions (attaching the alcohol instead of the acid to the steroid) changes the effect, E11-2,2rev is an agonist but E11-3,2rev is an antagonist. Whereas in the original esters, E11-2,2 is a strong antagonist and E11-3,2 is an agonist.

TABLE 2

| Structure | Label | Activity |
|---|---|---|
| 11β—CH$_2$OCH$_2$CH$_3$ | E11-1,2ether | agonist |
| 11β—CH$_2$OCH$_2$CH$_2$CH$_3$ | E11-1,3ether | strong antagonist |
| 11β—CH$_2$CH$_2$OCH$_3$ | E11-2,1ether | agonist/slight antagonist |
| 11β—CH$_2$CH$_2$OCH$_2$CH$_3$ | E11-2,2ether | strong antagonist |
| 11β—CH$_2$CH$_2$OCH$_2$CH$_2$CH$_3$ | E11-2,3ether | strong antagonist |
| 11β—CH$_2$CH$_2$OCH(CH$_3$)$_2$ | E11-2,iPr ether | strong antagonist |
| 11β—CH$_2$CH$_2$OC(CH$_3$)$_3$ | E11-2,tBu ether | very weak antagonist |
| 11β—CH$_2$CH$_2$O—cyclopropyl | E11-2,cyclo-Pr ether | strong antagonist |
| 11β—CH$_2$CH$_2$O—cyclopentyl | E11-2,cyclo-Pent ether | very strong antagonist |
| 11β—CH$_2$CH$_2$CH$_2$OCH$_3$ | E11-3,1 ether | antagonist |
| 11β—CH$_2$CH$_2$CH$_2$OCH$_2$CH$_3$ | E11-3,2 ether | strong antagonist |
| 11β—CH$_2$CH$_2$CH$_2$OCH$_2$CH$_2$F | E11-3,2F$_1$ ether | strong antagonist |
| 11β—CH$_2$CH$_2$CH$_2$OCH(CH$_3$)$_2$ | E11-3,iPr ether | strong antagonist |
| 11β—CH$_2$CH$_2$CH$_2$OC(CH$_3$)$_3$ | E11-3,tBu ether | very strong antagonist |
| 17α—C≡CH 11β—CH$_2$CH$_2$CH$_2$OCH(CH$_3$)$_2$ | 17α-ethynyl-E11-3,iPr ether | very strong antagonist |
| 17α—C≡CH 11β—CH$_2$CH$_2$CH$_2$OC(CH$_3$)$_3$ | 17α-ethynyl-E11-3,tBu ether | very strong antagonist |

Importantly, the entire ester function is not critical. Ethers (Table 2) and ketones (Table 1) are also antagonists. Note again that at least 5 (non-hydrogen) atoms are required in the 11β-sidechain for antagonism. Additionally the thionyl ester (thionyl esters are reported not to be hydrolyzed by esterases), E11-2S,2 is also a strong antagonist (Table 1). Some of the ethers are extremely strong antagonists, including the E11-2, cyclo-Pent ether and the E11-3,tBu ether. Introduction of the 17α-ethynyl group to protect against metabolic oxidation at C-17 produced 2 very strong antagonists: 17α-ethynyl-E11-3,tBu ether and 17α-ethynyl-E11-3,iPr ether. We expect that any of these compounds, the ketones, ethers thionoester, and especially the 17α-ethynyl compounds, will be orally active and this is to be tested.

In Vivo Uterotropic Activity

Figure 7:
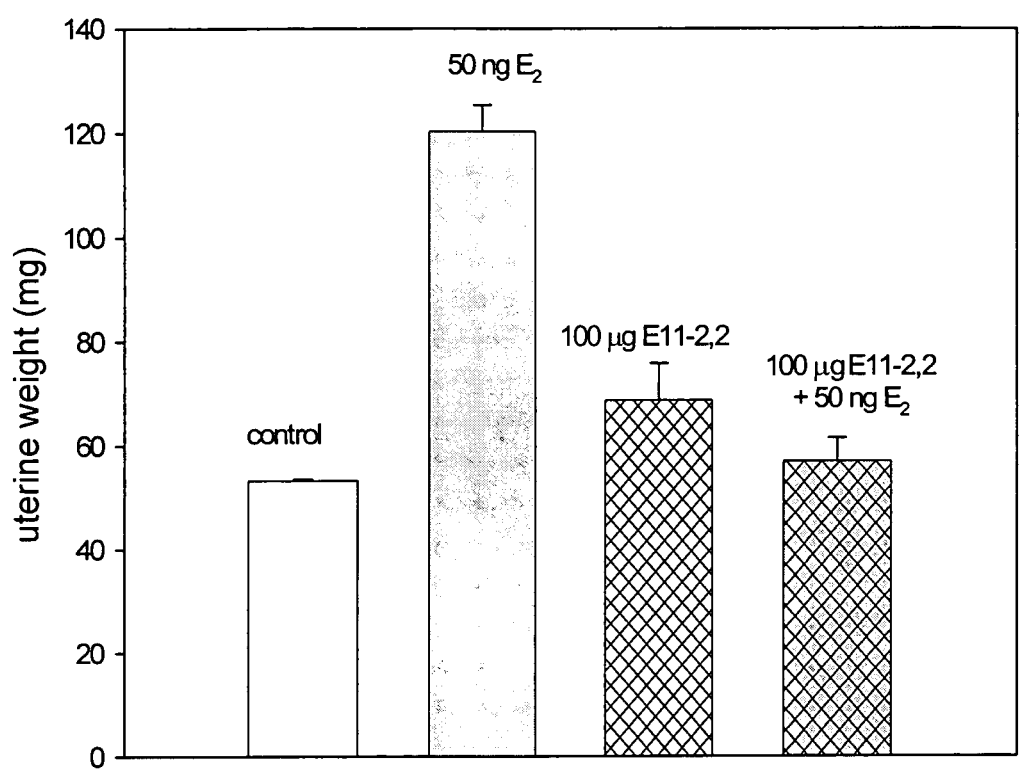
FIG. 7 shows the results of antiestrogenic action in an in vivo Uterotrophic Assay using immature female rats.

Finally, we have tested the antiestrogenic action of 3 of the analogs, the ester E11-2,2, the ether E11-2,2ether, and the ketone, E11-2,3K, by measuring their effect on the uterotrophic action of 20 ng of estradiol administered over 3 days in sesame oil to immature female rats. The analogs were administered concurrently in the same oil. One of the experiments, with 100 μg of the ester, E11-2,2 inhibiting the action of 50 ng of estradiol is shown in FIG. 7, in which the uterine weight is measured.

In other experiments not shown, E11-2,2 at 10 μg completely abolished the effect of 20 ng estradiol and was partially active at 3 μg. Although complete dose responses have not been performed yet, the ketone, E11-2,3K completely abolished the uterotrophic response of estradiol at a dose of 30 μg, while the ether, E11-2,2ether at that dose inhibited the effect of estradiol by about 50%.

The slight uterotrophic effect of these analogs as well as their small estrogenic effects in the Ishikawa cells is consistent with these compounds being SERMs rather than pure antiestrogens. While the mechanism by which these unusual antiestrogens work is not currently obvious, apparently groups that allow hydrogen bonding with a specific amino acid, likely in helix 12, are required. Further experiments on mechanism, including estrogen receptor modeling and x-ray crystallography of the analogs and the ligand binding domain (LBD) of the estrogen receptor are planned.

The invention claimed is:

1. A method of treating the symptomology of menopause in a patient while reducing the risk that the patient develops an estrogen-sensitive cancer, the method comprising administering to said patient an effective amount of a selective estrogen receptor modulator (SERM) which has the chemical structure:

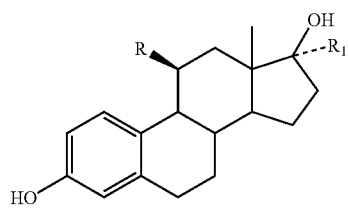

Where R is a sidechain group of at least 5 non-hydrogen atoms in length selected from a

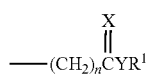

group, a

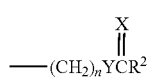

group, a

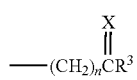

group, or a —(CH$_2$)$_n$XR$^4$ group,
R$^1$, R$^2$, R$^3$ and R$^4$ are each independently a C$_1$-C$_6$ linear, branch-chained or cyclo-alkyl group;
R$_1$ is H, CH$_3$, a vinyl group (—CH=CH$_2$), or an ethynyl group (—C≡CH);
X is O or S and Y is O; and n is from 1 to 3, wherein said symptomology is one or more of bone loss associated with osteoporosis, elevated cholesterol or elevated low-density lipoproteins (LDL), wherein said compound is other than compound E11-2, 2Rev of Table 1 and FIG. 8 having the chemical structure:

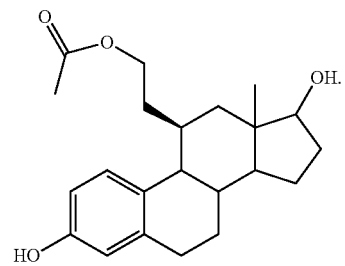

2. The method according to claim 1 wherein said menopausal symptomology is bone loss associated with osteoporosis.

3. The method according to claim 2 wherein R is an ester or thioester group and R$^1$ and R$^2$ are each independently a C$_1$-C$_5$ linear, branch-chained or cyclo-alkyl group.

4. The method according to claim 1 wherein said compound is orally administered to said patient and said estrogen-sensitive cancer is breast cancer.

5. The method according to claim 2 wherein said selective estrogen receptor modulator (SERM) is orally administered to said patient.

6. The method according to claim 3 wherein X is O.

7. The method according to claim 2 wherein X is O and R$_1$ is an ethynyl group.

8. The method according to claim 2 wherein when R is an ester group and n is 1, and R$^1$ and R$^2$ have at least two carbon atoms.

9. The method according to claim 2 wherein when R is a keto, thioketo, ether or thioether group, n is 1, and R$^3$ and R$^4$ have at least three carbon atoms.

10. The method according to claim 2 wherein said selective estrogen receptor modulator (SERM) is orally administered to said patient.

11. The method according to claim 3 wherein X is O.

12. The method according to claim 2 wherein X is O and R$_1$ is an ethynyl group.

13. The method according to claim 2 wherein when R is an ester group and n is 1, and R$^1$ and R$^2$ have at least two carbon atoms.

14. The method according to claim 2 wherein when R is a keto, thioketo, ether or thioether group, n is 1, and R$^3$ and R$^4$ have at least three carbon atoms.

15. A method of treating a patient suffering from an estrogen-sensitive cancer, the method comprising administering to said patient an effective amount of a selective estrogen receptor modulator (SERM) which has the chemical structure:

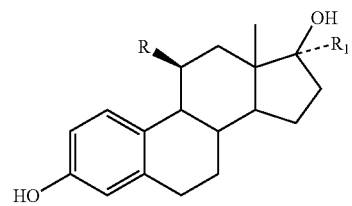

Where R is a sidechain group eat least 5 non-hydrogen atoms in length selected from a

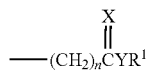

group, a

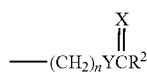

group, a

Figure 8:
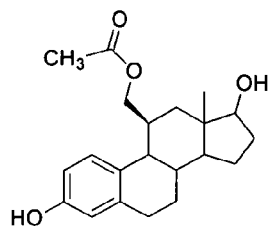
FIG. 8 exemplifies a number of compounds according to the present invention which are also depicted in Table 1 herein.
Figure 8:
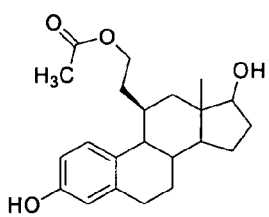
Figure 8:
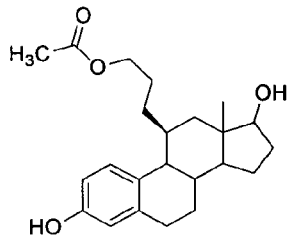
Figure 8:
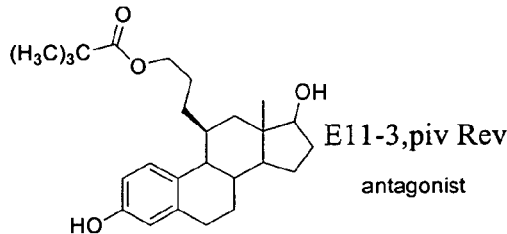
Figure 8:
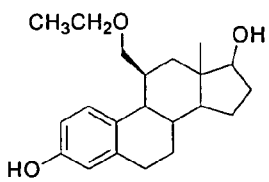
Figure 8:
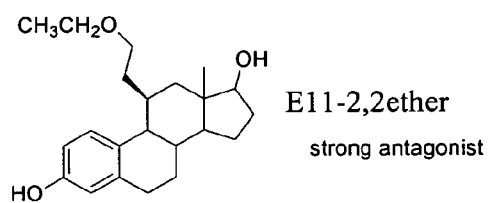
Figure 8:
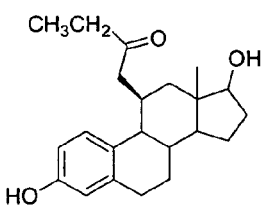
Figure 8:
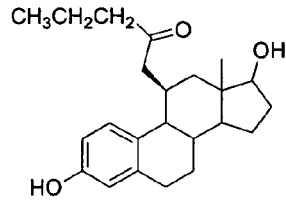
Figure 8:
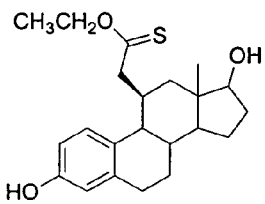
Figure 8:
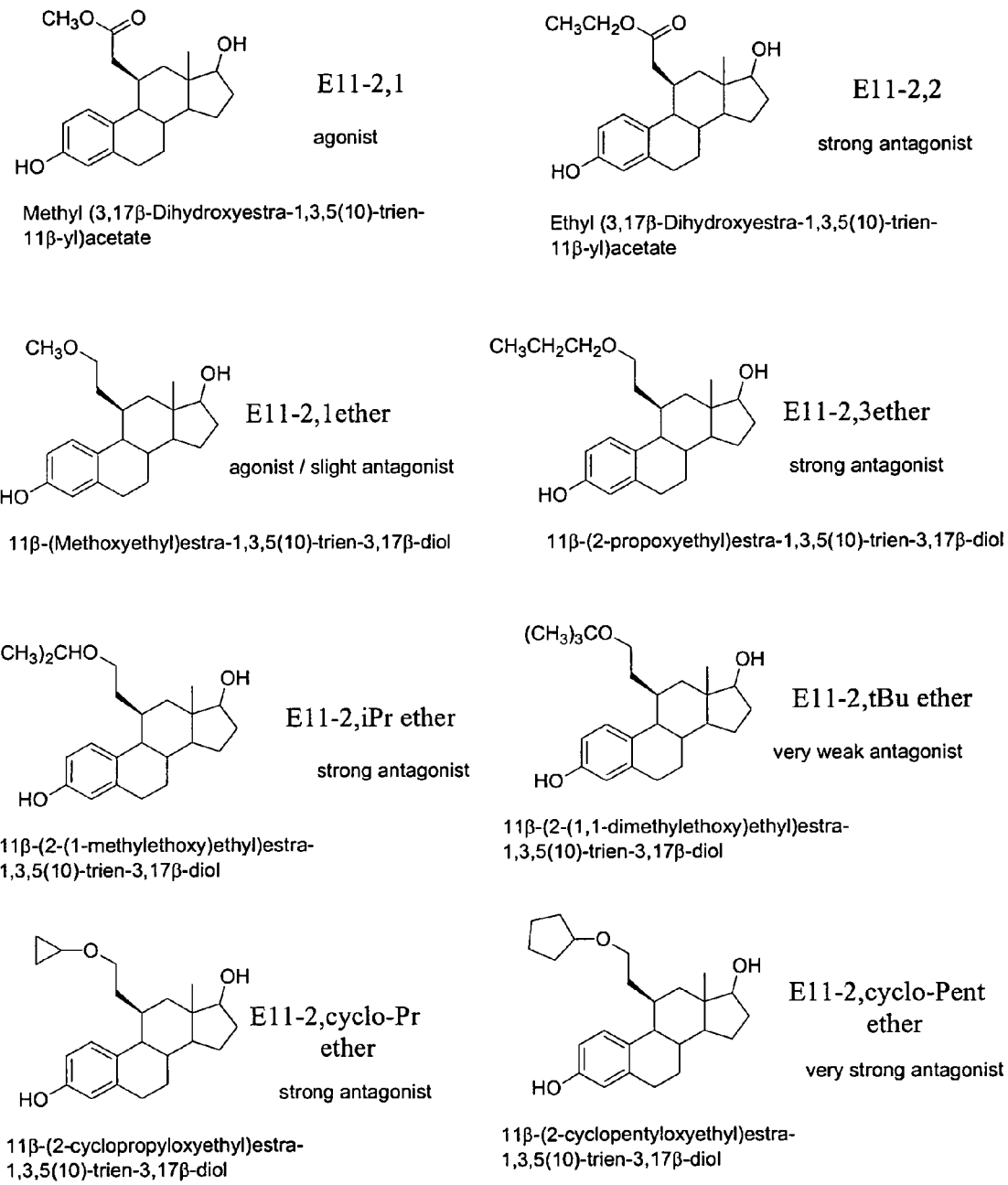
Figure 8:
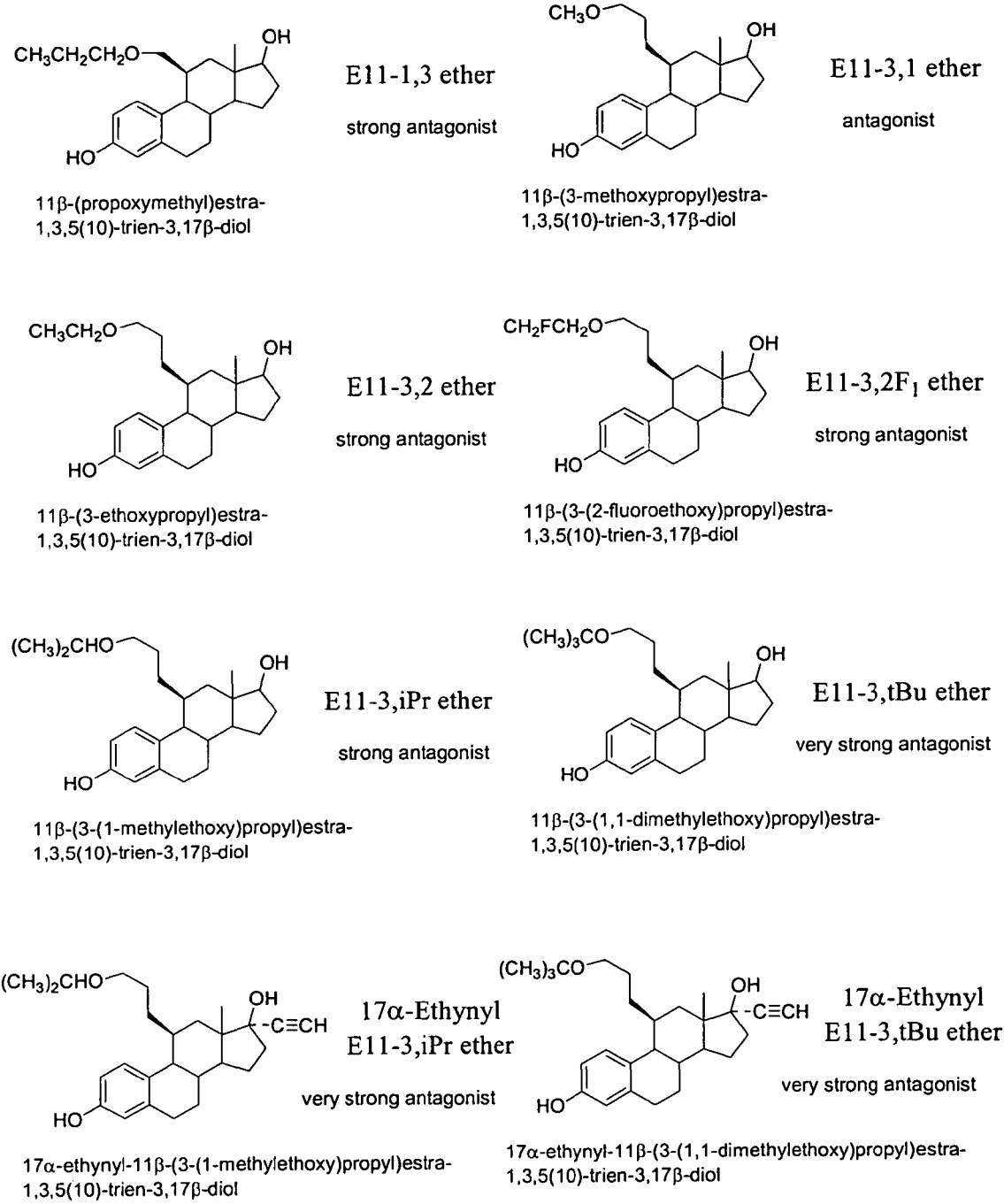

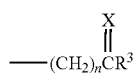

group, or a —(CH$_2$)$_n$XR$^4$ group,

R$^1$, R$^2$, R$^3$ and R$^4$ are each independently a C$_1$-C$_6$ linear, branch-chained or cyclo-alkyl group;

R$_1$ is H, CH$_3$, a vinyl group (—CH═CH$_2$), or an ethynyl group (—C≡CH);

X is O or S and Y is O; and n is from 1 to 3, wherein said compound is other than compound E11-2,2Rev of Table 1 and FIG. 8 having the chemical structure:

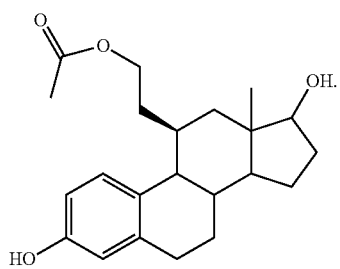 [SMILES: CC(=O)OCC[C@H]1CC2(C)C(O)CCC2C2CCc3cc(O)ccc3C21]

16. The method according to claim 15 wherein said estrogen-sensitive cancer is breast cancer.

17. The method according to claim 16 wherein R is an ester or thioester group and R$^1$ and R$^2$ are each independently a C$_1$-C$_5$ linear, branch-chained or cyclo-alkyl group.

18. The method according to claim 16 wherein said selective estrogen receptor modulator (SERM) is orally administered to said patient.

19. A method of treating the symptomology of menopause in a patient suffering from an estrogen-sensitive cancer, the method comprising administering to said patient an effective amount of a selective estrogen receptor modulator (SERM) which has the chemical structure:

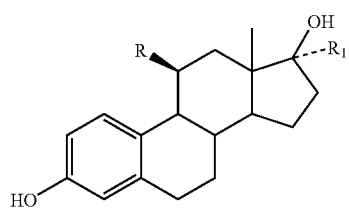

Where R is a sidechain group of at least 5 non-hydrogen atoms in length selected from a

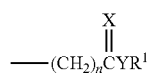

group, a

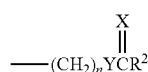

group, a

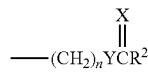

group, or a —(CH$_2$)$_n$XR$^4$ group,

R$^1$, R$^2$, R$^3$ and R$^4$ are each independently a C$_1$-C$_6$ linear, branch-chained or cyclo-alkyl group;

R$_1$ is H, CH$_3$, a vinyl group (—CH═CH$_2$), or an ethynyl group (—C≡CH);

X is O or S and Y is O;

n is from 1 to 3, wherein said symptomology of menopause is one or more of bone loss associated with osteoporosis, elevated cholesterol, or elevated low-density lipoproteins (LDL), and wherein said compound is other than compound E11-2,2Rev of Table 1 and FIG. 8 having the chemical structure:

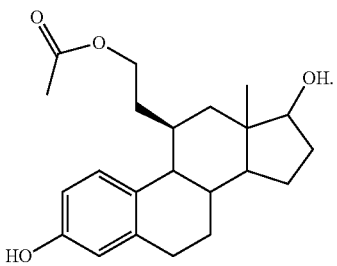

20. The method according to claim 19 wherein said menopausal symptomology is bone loss associated with osteoporosis.

21. The method according to claim 19 wherein wherein R is an ester or thioester group and R$^1$ and R$^2$ are each independently a C$_1$-C$_5$ linear, branch-chained or cyclo-alkyl group.

22. The method according to claim 19 wherein said selective estrogen receptor modulator (SERM) is orally administered to said patient.

23. The method according to claim 20 wherein said selective estrogen receptor modulator (SERM) is orally administered to said patient.

24. The method according to claim 19 wherein X is O.

25. The method according to claim 19 wherein X is O and $R_1$ is an ethynyl group.

26. The method according to claim 19 wherein when R is an ester group and n is 1, and $R^1$ and $R^2$ have at least two carbon atoms.

27. The method according to claim 19 wherein when R is a keto, thioketo, ether or thioether group, n is 1, and $R^3$ and $R^4$ have at least three carbon atoms.

28. The method according to claim 19 wherein said estrogen-sensitive cancer is breast cancer.

29. The method according to claim 20 wherein said estrogen-sensitive cancer is breast cancer.

\* \* \* \* \*